United States Patent [19]

Bremanis et al.

[11] Patent Number: 4,633,014
[45] Date of Patent: Dec. 30, 1986

[54] SUBSTITUTED 3-HYDRAZINOPROPIONATES

[75] Inventors: Gunar A. Bremanis, Jurmala; Ivars Y. Kalvinsh, Salaspils; Irene B. Antsena, Riga; Edmund Y. Lukevits, Riga; Maris M. Veveris, Riga; Valeryans Y. Kauss, Rizhsky raion Adazhi; Peter T. Trapentsier; Edvards E. Liepinsh, both of Riga, all of U.S.S.R.

[73] Assignee: Institut Organicheskogo Sinteza Akademii Nauk Latviiskoi Ssr

[21] Appl. No.: 628,240

[22] Filed: Jul. 6, 1984

[30] Foreign Application Priority Data

Jul. 13, 1983 [SU] U.S.S.R. ............... 3620453

[51] Int. Cl.$^4$ ............... C07C 157/05; C07C 157/07; C07C 157/09; C07C 153/057; C07C 133/02; C07C 127/15; C07C 127/17; C07C 127/19

[52] U.S. Cl. ............... 562/556; 564/78; 564/148; 564/149; 564/151; 558/393; 558/436; 558/441; 558/445; 560/16; 560/24; 560/34; 560/147; 560/148; 560/159; 560/169; 562/426; 562/439; 562/555; 562/560; 564/18; 564/34; 564/37; 564/74

[58] Field of Search ............ 562/556, 560, 426, 439, 562/555; 564/18, 34, 37, 74, 78, 149, 152; 560/169, 16, 24, 34, 137, 148, 147, 159; 260/465 D, 465.4

[56] References Cited

U.S. PATENT DOCUMENTS

| | | | |
|---|---|---|---|
| 2,658,062 | 11/1953 | Jones | 564/18 |
| 2,779,786 | 1/1957 | Coleman | 562/560 |
| 3,121,111 | 2/1964 | Berger | 562/556 |
| 3,129,258 | 4/1964 | Bloom | 560/169 |
| 3,318,680 | 5/1967 | Levitt | 564/18 |
| 3,888,840 | 6/1975 | Failli | 560/169 |

Primary Examiner—Michael L. Shippen
Attorney, Agent, or Firm—Ladas & Parry

[57] ABSTRACT

Substituted 3-hydrazinopropionates comprising compounds of the general formula:

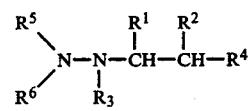

wherein $R^1$, $R^2$=H, an alkyl, a substituted alkyl, hydroxycarbonyl, alkoxycarbonyl, an aryl, an aralkyl, an unsaturated alkyl, a substituted aryl or a substituted aralkyl:

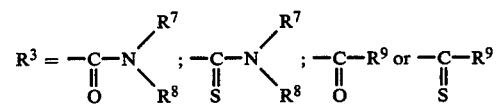

wherein
$R^7$, $R^8$=H, an alkyl, an unsaturated alkyl, an aralkyl, an aryl, a substituted alkyl,
$R^9$=OH, an alkoxy, an aralkoxy, an alkyl, an unsaturated alkyl, an aryl, a substituted aryl, an aralkyl;
$R^4$ is —C≡N, —COR$^{10}$, wherein $R^{10}$=OR$^{11}$, NR$^{12}$R$^{13}$, where $R^{11}$ is H, an alkyl, an aralkyl and an alkali metal, $R^{11}$ and $R^{12}$ are each H, an alkyl, an aralkyl, an aryl;
$R^5$, $R^6$= an alkyl, an aryl, an aralkyl.

4 Claims, No Drawings

SUBSTITUTED 3-HYDRAZINOPROPIONATES

FIELD OF THE INVENTION

The present invention relates to the organic chemistry and, more specifically, to novel substituted 3-hydrazinopropionates possessing an antiarrhythmic activity and useful in medicine for the treatment of the heart beat disturbances.

BACKGROUND OF THE INVENTION

Known in the art is rather wide range of a biological effect of close structural analogs of the compounds according to the present invention—hydrazides, semicarbazides, thiosemicarbazides. Thus, among these compounds there are antibacterial preparations known in the treatment of tuberculosis, monoaminooxydase inhibitors, analgetics, diuretics (cf. Mashkovsky M.D., Pharmaceutical Preparations, "Medicina" Publishing House, part 1, II, 1977). However, the literature fails to submit information to the effect that these compounds having such structure possess an antiarrhythmic activity.

The closest chemical structure is inherent in 1,1-dimethyl-2-methylcarbamoyl-2-(γ-phenylamyl)hydrazine, but no data on its biological activity are available in the literature (cf. K. Chantrapromma, W. D. Ollis, J. O. Sutherland, The thermal rearrangement of allyl- and pentadienyl-ammonioamidates. Evidence for competing but distinct concerted and radical mechanisms., J.Chem.Soc., Chem.Commun., 1977, (3), (97-99)).

The antiarrhythmic preparations currently employed in medicine—procaine amide and quinidine feature a high acute toxicity and bring about a number of negative side effects.

The present invention is directed to the provision of novel substituted 3-hydrazinopropionates possessing a high antiarrhythmic activity and a low toxicity.

The compounds according to the present invention are novel and hitherto unknown from the literature.

SUMMARY OF THE INVENTION

It is an object of the present invention to provide such novel substituted 3-hydrazinopropionates which would feature a high antiarrhythmic activity and a low toxicity.

These and other objects of the present invention are accomplished by such substituted 3-hydrazinopropionates which comprise compounds of the general formula:

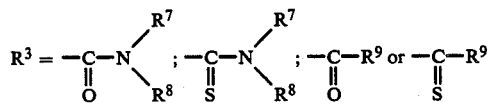

wherein $R^1$, $R^2$ = H, an alkyl, a substituted alkyl, hydroxycarbonyl, an alkoxycarbonyl, an aryl, an aralkyl, an unsaturated alkyl, a substituted aryl, or a substituted aralkyl;

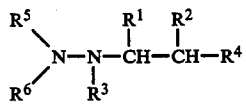

wherein $R^7$, $R^8$ = H, an alkyl, an unsaturated alkyl, an aralkyl, an aryl, a substituted alkyl;

$R^9$ is OH, an alkoxy, an aralkoxy, an alkyl, an unsaturated alkyl, an aryl, a substituted aryl, an aralkyl;

$R^4 = -C \equiv N$, $-COR^{10}$, wherein $R^{10} = OR^{11}$, $NR^{12}R^{13}$, where $R^{11}$ is H, an alkyl, an aralkyl, an alkali metal; $R^{12}$, $R^{13}$ are each H, an alkyl, an aralkyl, an aryl; $R^5$ and $R^6$ are an alkyl, an aryl, an aralkyl.

DETAILED DESCRIPTION OF THE INVENTION

Physico-chemical constants of the compounds according to the present invention are shown in Table 1.

The structure of substituted 3-hydrazinopropionates is justified by the data of elemental analysis (Table 2) and spectra of proton magnetic resonance (PMR) /Table 3/.

It is advisable to use substituted 3-hydrazinopropionates of the general formula:

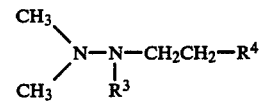

wherein in $R^3$=

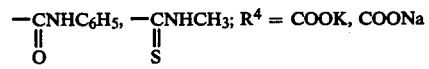

The study of the effect provided by the compounds according to the present invention on the cardio-vascular system was carried out in experiments on white mice. The specific (antiarrhythmic) effect and acute toxicity were studied. For the purpose of comparison known antiarrhythmic preparations—procaine amide and quinidine were used.

The antiarrhythmic activity of the compounds according to the present invention was studied on a model of arrhythmia induced by an intravenous administration of calcium chloride. In experiments on white mice of both sexes with a mass of 18-25 g narcotized by urethane (1,200 mg/kg intraperitoneally) ECG in the second standard lead was recorded. A 2% solution of calcium chloride was introduced into the tail vein at a constant rate (0.01 ml for 2 sec). The dose of calcium chloride causing arrhythmia and the dose causing the heart arrest were determined. In the test groups the test compounds were administered intraperitoneally 20-40 minutes before the beginning of the experiment. The results thus obtained are given in Table 4.

As it follows from the data of the above Table 4, the compounds according to the present invention possess the antiarrhythmic activity comparable with that of highly effective clinical preparations—quinidine and procaine amide.

The acute toxicity of the compounds according to the present invention was determined in experiments on white mice with a mass of 20-25 g. The test compounds were administered intraperitoneally in the form of aqueous solutions or suspensions in Twin-80. Observation over the test animals was effected for 10 days. The results thus obtained are shown in Table 5. It has been found that the compounds according to the present invention are low-toxic. As compared to quinidine they have a substantially lower toxicity which is demonstrated by high figures of the relative toxicity (Table 5).

Therefore, it has been found that the compounds according to the present invention possess a considerable antiarrhythmic activity and a substantially lower toxicity which distinguishes them favourably from the known preparations. This enables a suggestion that the compounds according to the present invention will be useful in medicine.

The method for the preparation of substituted 3-hydrazino propionates is rather simple.

The compounds according to the present invention are produced by a known procedure by reacting substituted 3-(2,2-disubstituted hydrazino)propionates with isocyanates, isothiocyanates or acylation agents. If it is necessary to introduce an amide grouping, the compounds produced by the above-mentioned reactions are subjected to ammonolysis; when required to obtain free acids or salts thereof, these compounds are subjected to hydrolysis.

For a better understanding of the present invention some specific examples are given hereinbelow.

EXAMPLE 1

3-(2,2-Dimethyl-1-carbamoylhydrazino)-methylpropionate (I-I)

To a solution of 0.86 g (0.01 mol) of tetraisocyanatosilane in 10 ml of absolute benzene 2.92 (0.02 mol) of 3-(2,2-dimethylhydrazino)-methylpropionate are added and allowed to stand at room temperature for 12 hours. Then the reaction mixture is brought to boiling and 5 ml of an aqueous solution of acetonitrile is dropwise added thereto. The residue is separated, the filtrate is evaporated to dryness, added with isopropanol and evaporated once more. The residue is distilled at a temperature of 88°–95° C. ($10^{-2}$ mm Hg) to give 0.75 g (20%) of colourless crystals of 3-(2,2-dimethyl-1-carbamoylhydrazino)-methylpropionate (I-I) melting at 63°–64° C. The data of its elemental analysis and spectral characteristics are shown in Tables 1, 2 and 3.

In a manner similar to the production of 3-(2,2-dimethyl-1-carbamoylhydrazino)-methylpropionate there is obtained 3-(2,2-dimethyl-1-carbamoylhydrazino)-2-methyl-methylpropionate (I-II) from 3-(2,2-dimethylhydrazino)-2-methyl-methylpropionate and tetraisocyanatosilane.

EXAMPLE 2

3-(2,2-Dimethyl-1-methylcarbamoylhydrazino)-methylpropionate (I-2)

To a solution of 14.6 g (0.1 mol) of 3-(2,2-dimethylhydrazino)-methylpropionate in 10 ml of acetonitrile 5.7 g (0.1 mol) of methylisocyanate in anhydrous acetonitrile (10 ml) are added and kept at the boiling temperature of the solvent for 6 hours. The solvent is then removed and the residue is crystallized from isopropanol to give 11.6 g (57%) of colourless crystals of 3-(2,2-dimethyl-1-methylcarbamoylhydrazino)-methylpropionate (I-2) melting at 77°–78° C.

In a similar manner from respective iso- and isothiocyanates the following compounds are prepared:

3-(2,2-dimethyl-1-phenylcarbamoylhydrazino)-methylpropionate (I-3);

3-(2,2-dimethyl-1-p-/2-dimethylamino-2-methylpropionato-2'-yl-ureido-1-yl/anilinocarbanylhydrazino)-methylpropionate (I-4);

3-(2,2-dimethyl-1-methylthiocarbamoylhydrazino)methylpropionate (I-5);

3-(2,2-dimethyl-1-allylthiocarbamoylhydrazino)methylpropionate (I-6);

3-(2,2-dimethyl-1-phenylthiocarbamoylhydrazino)methylpropionate (I-7);

3-(2,2-dimethyl-1-methylcarbamoylhydrazino)-ethylpropionate (I-8);

3-(2,2-dimethyl-1-allylthiocarbamoylhydrazino)ethylpropionate (I-9);

3-(2,2-dimethyl-1-phenylthiocarbamoylhydrazino)ethylpropionate (I-10);

3-(2,2-dimethyl-1-methylcarbamoylhydrazino)-2-methyl-methylpropionate (I-12);

3-(2,2-dimethyl-1-allylthiocarbamoylhydrazino)-2-methyl-methylpropionate (I-13);

3-(2,2-dimethyl-1-phenylthiocarbamoylhydrazino)methylpropionate (I-14);

3-(2,2-dimethyl-1-methylcarbamoylhydrazino)propionitrile (I-21);

3-(2,2-dimethyl-1-allylthiocarbamoylhydrazino)propionitrile (I-22);

3-(2,2-dimethyl-1-phenylthiocarbamoylhydrazino)propionitrile (I-23);

3-(2,2-dimethyl-1-methylcarbamoylhydrazino)-2-methoxycarbonylmethylpropionate (I-55);

3-(2,2-dimethyl-1-phenylcarbamoylhydrazino)-2-methoxycarbonylmethylpropionate (I-56);

3-(2,2-dimethyl-1-/ε-(2-dimethylamino-2-dimethylsuccinato-2'-ylureido-1-yl)hexylcarbamoyl/hydrazino)-2-methoxycarbonylmethylpropionate (I-57);

3-(2,2-dimethyl-1-phenylthiocarbamoylhydrazino)octylpropionate (I-60);

3-(2,2-dimethyl-1-phenylcarbamoylhydrazino)propionitrile (I-61); (see Tables 1,2 and 3).

EXAMPLE 3

3-(2,2-dimethyl-1-methylcarbamoylhydrazino)-propionamide (I-15)

To a suspension of 0.32 g (0.1 mol) of the compound I-2 produced as described in Example 2 in ethanol (25 ml) 85 ml (5.0 mol) of liquid ammonia are added and the reaction mixture is kept in an autoclave at room temperature for 170 hours. The excess of ammonia is evaporated, the residues is filtered and washed with acetone to give 13.5 g (71.7%) of 3-(2,2-dimethyl-1-carbamoylhydrazino)propionamide (I-15) with the melting point of 173°–173.5° C. (tables 2 and 3).

In a similar manner the following compounds are obtained:

3-(2,2-dimethylamino-1-phenylcarbamoylhydrazino)-propionamide (I-16);

3-(2,2-dimethylamino-1-methylthiocarbamoylhydrazino)propionamide (I-17);

3-(2,2-dimethyl-1-amylthiocarbamoylhydrazino)propionamide (I-18);

3-(2,2-dimethyl-1-phenylthiocarbamoylhydrazino)propionamide (I-19);

3-(2,2-dimethyl-1-phenylthiocarbamoylhydrazino)2-methylpropionamide (I-20).

This procedure also makes it possible to produce, from respective acylhydrazines, the following compounds:

3-(2,2-dimethyl-1-acetylhydrazino)propionamide (I-47);

3-(2,2-dimethyl-1-butyrylhydrazino)propionamide (I-48);

3-(2,2-dimethyl-1-hexanoylhydrazino)propionamide (I-49);
3-(2,2-dimethyl-1-octadecanoylhydrazino)propionamide (I-50);
3-(2,2-dimethyl-1-benzoylhydrazino)propionamide (I-51);
3-(2,2-dimethyl-1-γ-hydroxypropanoylhydrazino)propionamide (I-52);
3-(2,2-dimethyl-1methoxycarbonylhydrazino)propionamide (I-53).

EXAMPLE 4

3-(2,2-Dimethyl-1-acetylhydrazino)methylpropionate (I-24)

To a solution of 7.85 g (0.1 mol) of acetyl chloride in 25 ml of dry methylethylketone at the temperature of −40° C. a solution of 15.6 g (0.1 mol) of 3-(2,2-dimethylhydrazino)-methylpropionate in 30 ml of dry methylethylketone is dropwise added along with 10.12 g (0.1 mol) of triethylamine. The reaction mixture is stirred for 2 hours at the temperature of −40° C., then during 2 hours the temperature is elevated to room temperature and stirring is continued for additional 12 hours. The residue is filtered the filtrate is added with water and carbon tetrachloride. The aqueous layer is separated and several times extracted with carbon tetrachloride (250 ml in total). The solution of carbon tetrachloride is dried by anhydrous sodium sulphate and the solvent is removed. The residue is distilled at the temperature of 74° C. ($7.10^{-2}$ mm Hg) to give 10.4 g (55%) of 3-(2,2-dimethyl-1-acetylhydrazino)-methylpropionate (I-24).

In a similar manner the following compounds are obtained:

3-(2,2-dimethyl-1-butyrylhydrazino)-methylpropionate (I-25);
3-(2,2-dimethyl-1-hexanoylhydrazino)methylpropionate (I-26)
3-(2,2-dimethyl-1-hexadecanoylhydrazino)methylpropionate (I-27)
3-(2,2-dimethyl-1-octadecanoylhydrazino)methylpropionate (I-28);
3-(2,2-dimethyl-1-benzoylhydrazino)methylpropionate (I-29);
3-(2,2-dimethyl-1-benzylcarbonylhydrazino)methylpropionate (I-30);
3-(2,2-dimethyl-I-(2'-fluorophenylcarbonyl)hydrazino)-methylpropionate (I-31);
3-(2,2-dimethyl-1-(4'-bromophenylcarbonyl)hydrazino)methylpropionate (I-32);
3-(2,2-dimethyl-1-(2'-benzoyloxymethyl)benzylhydrazino)methylpropionate (I-33);
3-(2,2-dimethyl-1-acroylhydrazino)-methylpropionate (I-34);
3-(2,2-dimethyl-1-methoxycarbonylhydrazino)methylpropionate (I-36);
3-(2,2-dimethyl-I-acetylhydrazino)-2-methylmethylpropionate (I-37);
3-(2,2-dimethyl-1-hexanoylhydrazino)-2-methylmethylpropionate (I-38);
3-(2,2-dimethyl-1-benzoylhydrazino)-2-methylmethylpropionate (I-39);
3-(2,2-dimethyl-1-2'-fluorobenzoylhydrazino)-2-methylmethylpropionate (I-40);
3-(2,2-dimethyl1-4'-bromobenzoylhydrazino)-2-methylpropionate (I-41);
3-(2,2-dimethyl-1-acetylhydrazino)ethylpropionate (I-42);
3-(2,2-dimethyl-1-hexanoylhydrazino)ethylpropionate (I-43);
3-(2,2-dimethyl-1-benzoylhydrazino)ethylpropionate (I-44);
3-/2,2-dimethyl-1-(2'-fluorobenzoyl)-hydrazino/ethylpropionate (I-45);
3-/2,2-dimethyl-1-(4'-bromobenzoyl)hydrazino/ethylpropionate (I-46);
3-(2,2-dimethyl-1-benzoylhydrazino)propionitrile (I-54);
3-(2,2-dimethyl-1-benzoylhydrazino)-3-methoxycarbonyl-methylpropionate (I-58);
3-(2,2-dimethyl-1-propionylhydrazino)-propionitrile (I-62);
3-(2,2-dimethyl-1-2'-fluorobenzoylhydrazino)propionitrile (I-63);

EXAMPLE 5

3-(2,2-Dimethyl-1-3'-hydroxypropanoylhydrazino)-methylpropionate (I-35)

To a solution of 73.1 g (0.5 mol) of 3-(2,2-dimethylhydrazino)methylpropionate in 25 ml of absolute acetonitrile at the temperature of 5° C. 36.03 g (0.5 mol) of propiolactone in 25 ml of absolute acetonitrile are added. Then the temperature is increased to room temperature for 2 hours and the reaction mixture is stirred for 2 hours. The formed precipitate (62.47 g, 57%) is filtered and crystallized from methanol-acetone (1:2) with gradual addition of acetone prior to the beginning of crystallization to obtain colourless crystals of 3-/2,2-dimethyl-1-(3-hydroxypropanoyl)hydrazino/methylpropionate (I-49) with the melting temperature of 124°–126° C. (Tables 1, 2 and 3).

EXAMPLE 6

Sodium salt of 3-(2,2-dimethyl-1-methylthiocarbamoylhydrazino)propionate (I-59)

6.6 g (0.03 mol) of the compound I-5 prepared as in Example 2 hereinbefore are suspended in a solution of 3.15 g of sodium carbonate in 30 ml of water and stirred for 48 hours. The reaction mass is added with 15 ml of ethanol and stirred for 12 hours, the residue is filtered-off, added with isopropanol and ethanol and filtration is performed once more. The mother liquor is evaporated to dryness to give 2.69 g (39.5%) of a soium salt of 3-(2,2-dimethyl-1-methylthiocarbamoylhydrazino)-propionate (I-59), see Tables 1, 2 and 3.

EXAMPLE 7

Potassium salt of 3-(2,2-dimethyl-1-phenylcarbamoylhydrazino)-methylpropionate (I-64)

A suspension of 4.78 g (0.018 mol) of 3-(2,2-dimethyl-1-phenylcarbamoylhydrazino)methylpropionate (I-3) in a solution of 1.01 g (0.018 mol) of potassium hydroxide in 20 ml of water is stirred upon heating to a complete dissolution. The solution is evaporated in a rotary evaporator, the residue is dissolved in isopropanol, evaporated (to remove the residual water), dissolved in acetonitrile and then ether is added to the product till it gets turbid. The colourless crystals precipitated upon standing are filtered, washed with ether and vacuum-dried at room temperature over $P_2O_5$ to give 3.0 g of a colourless powder (54.2% of the theoretical) /see Tables 1,2 and 3/. In the determination of the melting point the product dissolves in its own crystal-hydrate water at a temperature of 50°-55° C.

EXAMPLE 8

3-/2,2-Dimethyl-1-carbamoylhydrazino/propionamide (I-66)

To a solution of 72.5 g (0.55 mol) of 3-(2,2-dimethyl-hydrazino)propionamide in water a solution of 44.8 g (0.55 mol) of potassium cyanate is added. Upon stirring, the mixture is added with a concentrated hydrochloric acid till the neutral reaction (pH 7-8). The reaction mixture is allowed to stand for 12 hours at room temperature, whereafter it is evaporated to dryness. After treatment of the residue with isopropanol and a repeated evaporation a solid residue is obtained. The residue is boiled with ethanol and, after evaporation of the mother liquors, 40.0 g (42%) of colourless crystals of 3-(2,2-dimethyl-1-carbamoylhydrazino)propionamide with the melting point of 170°-172° C. are obtained.

After recrystallization from ethanol colourless crystals melting at 171°-172° C. are obtained.

In a similar matter, using sodium thioisocyanate, 3-(2,2-dimethyl-1-thiocarbamoylhydrazino)methylpropionate (I-67) is obtained. (See Tables 1, 2 and 3).

EXAMPLE 9

3-(2,2-Dimethyl-1-carbamoylhydrazino)propionic acid (I-65)

To a solution of 0.95 g (0.005 mol) of 3-(2,2-dimethyl-1-carbamoylhydrazino)methylpropionate (I-2) in 2 ml of water 1 drop of a concentrated hydrochloric acid is added. The mixture is heated to obtain a viscous mass which is allowed to stand at room temperature for 12 hours. Then the residue is treated with isopropanol. After a repeated evaporation colourless crystals are obtained which are filtered-off and dried at the temperature of 50° C. After crystallization 0.60 g (68%) of colourless crystals is obtained comprising 3-(2,2-dimethyl-1-carbamoylhydrazino)propionic acid melting at 171°-172° C.

TABLE 1

Physico-chemical constants of compounds having the general formula I

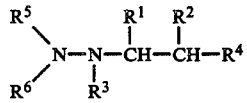

| Designated compounds | $R^1$ | $R^2$ | $R^3$ | $R^4$ | $R^5$ | $R^6$ | t° of boiling/pressure (°C./mm Hg) | t° of melting (°C.) |
|---|---|---|---|---|---|---|---|---|
| 1 | 2 | 3 | 4 | 5 | 6 | 7 | 8 | 9 |
| I-1 | H | | $CONH_2$ | $COOCH_3$ | $CH_3$ | $CH_3$ | | 63-64 |
| I-2 | H | H | $CONHCH_3$ | $COOCH_3$ | $CH_3$ | $CH_3$ | | 77-78 |
| I-3 | H | | $CONHC_6H_5$ | $COOCH_3$ | $CH_3$ | $CH_3$ | 173/0,2 | |
| I-4 | H | H | $CONHC_6H_4$—p-NH\|$H_3COOCCH_2CH_2NCO$\|$N(CH_3)_2$ | $COOCH_3$ | $CH_3$ | $CH_3$ | | 174-175,5 |
| I-5 | H | H | $CSNHCH_3$ | $COOCH_3$ | $CH_3$ | $CH_3$ | | 73,5-75,5 |
| I-6 | H | H | $CSNHCH_2CH=CH_2$ | $COOCH_3$ | $CH_3$ | $CH_3$ | | 54,5-56 |
| I-7 | H | H | $CSNC_6H_5$ | $COOCH_3$ | $CH_3$ | $CH_3$ | | 78,5-80 |
| I-8 | H | H | $CONHCH_3$ | $COOC_2H_5$ | $CH_3$ | $CH_3$ | 93/0,005 | |
| I-9 | H | H | $CSNHCH_2CH=CH_2$ | $COOC_2H_5$ | $CH_3$ | $CH_3$ | 155-165/0,005 | |
| I-10 | H | H | $CSNHC_6H_5$ | $COOC_2H_5$ | $CH_3$ | $CH_3$ | | 51-53 |
| I-11 | H | $CH_3$ | $CONH_2$ | $COOCH_3$ | $CH_3$ | $CH_3$ | | 96-97 |
| I-12 | H | $CH_3$ | $CONHCH_3$ | $COOCH_3$ | $CH_3$ | $CH_3$ | 109-119/0,005 | |
| I-13 | H | $CH_3$ | $CSNHCH_2CH=CH_2$ | $COOCH_3$ | $CH_3$ | $CH_3$ | 120-137/0,005 | |
| I-14 | H | $CH_3$ | $CSNHC_6H_5$ | $COOCH_3$ | $CH_3$ | $CH_3$ | | 62,5-65 |
| I-15 | H | H | $CONHCH_3$ | $CONH_2$ | $CH_3$ | $CH_3$ | | 173-173,5 |
| I-16 | H | H | $CONHC_6H_5$ | $CONH_2$ | $CH_3$ | $CH_3$ | | 156-157 |
| I-17 | H | H | $CSNHCH_3$ | $CONH_2$ | $CH_3$ | $CH_3$ | | 109-109,5 |
| I-18 | H | H | $CSNHCH_2CH=CH_2$ | $CONH_2$ | $CH_3$ | $CH_3$ | | 100,5-101 |
| I-19 | H | H | $CSNHC_6H_5$ | $CONH_2$ | $CH_3$ | $CH_3$ | | 154-155 |
| I-20 | H | $CH_3$ | $CSNHC_6H_5$ | $CONH_2$ | $CH_3$ | $CH_3$ | | 127-128 |
| I-21 | H | H | $CONHCH_3$ | CN | $CH_3$ | $CH_3$ | | 75-78 |
| I-22 | H | H | $CSNHCH_2CH=CH_2$ | CN | $CH_3$ | $CH_3$ | | 65-67 |
| I-23 | H | H | $CSNHC_6H_5$ | CN | $CH_3$ | $CH_3$ | | 102-103 |
| I-24 | H | H | $COCH_3$ | $COOCH_3$ | $CH_3$ | $CH_3$ | 74/0,07 | |
| I-25 | H | H | $COCH_2CH_2CH_3$ | $COOCH_3$ | $CH_3$ | $CH_3$ | 84-91/0,05 | |
| I-26 | H | H | $CO(CH_2)_4CH_3$ | $COOCH_3$ | $CH_3$ | $CH_3$ | 136/0,08 | |
| I-27 | H | H | $CO(CH_2)_{14}CH_3$ | $COOCH_3$ | $CH_3$ | $CH_3$ | | 30-34,5 |
| I-28 | H | H | $CO(CH_2)_{16}CH_3$ | $COOCH_3$ | $CH_3$ | $CH_3$ | | 42-44 |
| I-29 | H | H | $COC_6H_5$ | $COOCH_3$ | $CH_3$ | $CH_3$ | | 41-43 |
| I-30 | H | H | $COCH_2C_6H_5$ | $COOCH_3$ | $CH_3$ | $CH_3$ | 1,502* oil | |
| I-31 | H | H | $COC_6H_4F$—o | $COOCH_3$ | $CH_3$ | $CH_3$ | 1,508* oil | |
| I-32 | H | H | $COC_6H_4Br$—n | $COOCH_3$ | $CH_3$ | $CH_3$ | | 57,5-58,5 |
| I-33 | H | H | $COC_6H_4$—o-$CH_2OCOC_6H_5$ | $COOCH_3$ | $CH_3$ | $CH_3$ | | 93-94 |
| I-34 | H | H | $COCH=CH_2$ | $COOCH_3$ | $CH_3$ | $CH_3$ | oil | |
| I-35 | H | H | $COOCH_2CH_2OH$ | $COOCH_3$ | $CH_3$ | $CH_3$ | | 124-126 |

TABLE 1-continued
Physico-chemical constants of compounds having the general formula I $$R^5\text{-}N(R^6)\text{-}N(R^3)\text{-}CH(R^1)\text{-}CH(R^2)\text{-}R^4$$

| Designated compounds 1 | $R^1$ 2 | $R^2$ 3 | $R^3$ 4 | $R^4$ 5 | $R^5$ 6 | $R^6$ 7 | t° of boiling/pressure (°C./mm Hg) 8 | t° of melting (°C.) 9 |
|---|---|---|---|---|---|---|---|---|
| I-36 | H | H | COOCH$_3$ | COOCH$_3$ | CH$_3$ | CH$_3$ | 69/0.1 | |
| I-37 | H | CH$_3$ | COCH$_3$ | COOCH$_3$ | CH$_3$ | CH$_3$ | 130-152/0,5 | |
| I-38 | H | CH$_3$ | CO(CH$_2$)$_4$CH$_3$ | COOCH$_3$ | CH$_3$ | CH$_3$ | 1,456* | |
| I-39 | H | CH$_3$ | COC$_6$H$_5$ | COOCH$_3$ | CH$_3$ | CH$_3$ | 88-106/0,005 | |
| I-40 | H | CH$_3$ | COC$_6$H$_4$F—o | COOCH$_3$ | CH$_3$ | CH$_3$ | | 64.5-66 |
| I-41 | H | CH$_3$ | COC$_6$H$_4$Br—n | COOCH$_3$ | CH$_3$ | CH$_3$ | 123-143/0,005 | |
| I-42 | H | H | COCH$_3$ | COOC$_2$H$_5$ | CH$_3$ | CH$_3$ | 104/0,5 | |
| I-43 | H | H | CO(CH$_2$)$_4$CH$_3$ | COOC$_2$H$_5$ | CH$_3$ | CH$_3$ | 1,455* oil; | |
| I-44 | H | H | COC$_6$H$_5$ | COOC$_2$H$_5$ | CH$_3$ | CH$_3$ | 1,502* oil; | |
| I-45 | H | H | COC$_6$H$_4$F—o | COOC$_2$H$_5$ | CH$_3$ | CH$_3$ | | 53-55,5 |
| I-46 | H | H | COC$_6$H$_4$Br—n | COOC$_2$H$_5$ | CH$_3$ | CH$_3$ | 1,540* oil; | |
| I-47 | H | H | COCH$_3$ | CONH$_2$ | CH$_3$ | CH$_3$ | | 142-142,5 |
| I-48 | H | H | CO(CH$_2$)$_2$CH$_3$ | CONH$_2$ | CH$_3$ | CH$_3$ | | 108-108,5 |
| I-49 | H | H | CO(CH$_2$)$_4$CH$_3$ | CONH$_2$ | CH$_3$ | CH$_3$ | | 59-60 |
| I-50 | H | H | CO(CH$_2$)$_{16}$CH$_3$ | CONH$_2$ | CH$_3$ | CH$_3$ | | 76-77,5 |
| I-51 | H | H | COC$_6$H$_5$ | CONH$_2$ | CH$_3$ | CH$_3$ | | 144,5-145,5 |
| I-52 | H | H | COCH$_2$CH$_2$OH | CONH$_2$ | CH$_3$ | CH$_3$ | | 142,5-143 |
| I-53 | H | H | COOCH$_3$ | CONH$_2$ | CH$_3$ | CH$_3$ | 1,483* oil; | |
| I-54 | H | H | COC$_6$H$_5$ | CN | CH$_3$ | CH$_3$ | 105/0,006 | |
| I-55 | COOCH$_3$ | H | CONHCH$_3$ | COOCH$_3$ | CH$_3$ | CH$_3$ | 120-125/0.005 | |
| I-56 | COOCH$_3$ | H | CONHC$_6$H$_5$ | COOCH$_3$ | CH$_3$ | CH$_3$ | | 117-119 |
| I-57 | COOCH$_3$ | H | CONH(CH$_2$)$_6$—NH—CO—N((CH$_3$)$_2$)—N—CH(COOCH$_3$)—CH$_2$COOCH$_3$ | COOCH$_3$ | CH$_3$ | CH$_3$ | | 91-94 |
| I-58 | COOCH$_3$ | H | COC$_6$H$_5$ | COOCH$_3$ | CH$_3$ | CH$_3$ | | 116-117 |
| I-59 | H | H | CSNHCH$_3$ | COONa | CH$_3$ | CH$_3$ | | 140 |
| I-60 | H | H | CSNHC$_6$H$_5$ | COOC$_8$H$_{17}$ | CH$_3$ | CH$_3$ | 1.502* 78/0.006 | |
| I-61 | H | H | CONHC$_6$H$_5$ | CN | CH$_3$ | CH$_3$ | | |
| I-62 | H | H | COCH$_2$CH$_3$ | CN | CH$_3$ | CH$_3$ | 1.461* 77-8/0.002 | |
| I-63 | H | H | COCH$_2$CH$_3$ | CN | CH$_3$ | CH$_3$ | | 52 |
| I-64 | H | H | C(O)—NHC$_6$H$_5$ | COOK | CH$_3$ | CH$_3$ | | 50-55 |
| I-65 | H | H | CONH$_2$ | COOH | CH$_3$ | CH$_3$ | | 171-172 |
| I-66 | H | H | CONH$_2$ | CONH$_2$ | CH$_3$ | CH$_3$ | | 171-172 |
| I-67 | H | H | CSNH$_2$ | COOCH$_3$ | CH$_3$ | CH$_3$ | 85-95/7.10$^{-3}$ | |
| I-68 | COOCH$_3$ | H | CSNHCH$_2$CH=CH$_2$ | COOCH$_3$ | CH$_3$ | CH$_3$ | | 79-80 |
| I-69 | H | H | CONHCH$_2$CH$_2$CH$_2$CH$_3$ | CONH$_2$ | CH$_3$ | CH$_3$ | | 128-129 |

*Refractive index $n_D^{20}$

TABLE 2
Elementary analysis data and yield of the compounds I

| Designated Compounds 1 | Found, % C 2 | H 3 | N 4 | Calculated, % C 5 | H 6 | N 7 | Yield, (%) 8 |
|---|---|---|---|---|---|---|---|
| I-1 | 44,71 | 7,95 | 21,43 | 44,43 | 7,99 | 22,21 | 19,9 |
| I-2 | 46,98 | 8,65 | 20,42 | 47,27 | 8,43 | 20,68 | 91,3 |
| I-3 | 58,71 | 7,12 | 16,10 | 58,85 | 7,22 | 15,84 | 89,7 |
| I-4 | 53,22 | 7,30 | 18,48 | 53,08 | 7,13 | 18,57 | 68,5 |
| I-5 | 43,58 | 7,55 | 18,91 | 43,81 | 7,81 | 19,16 | 94,2 |
| I-6 | 49,22 | 7,90 | 17,06 | 48,95 | 7,81 | 17,13 | 81,6 |
| I-7 | 55,29 | 6,68 | 14,64 | 55,49 | 6,81 | 14,93 | 84,0 |
| I-8 | 50,04 | 8,65 | 19,34 | 50,22 | 8,89 | 19,52 | 72,6 |
| I-9 | 51,18 | 7,61 | 16,52 | 51,34 | 7,44 | 16,33 | 65,3 |
| I-10 | 56,82 | 6,99 | 14,07 | 56,92 | 7,17 | 14,23 | 99,0 |
| I-11 | 47,13 | 8,28 | 20,42 | 47,27 | 8,43 | 20,68 | 20,9 |
| I-12 | 49,59 | 9,03 | 19,06 | 49,75 | 8,82 | 19,34 | 92,8 |
| I-13 | 51,21 | 7,98 | 16,43 | 50,94 | 8,16 | 16,20 | 88,8 |
| I-14 | 56,76 | 7,06 | 14,09 | 56,92 | 7,17 | 14,23 | 58,2 |
| I-15 | 44,64 | 8,52 | 30,05 | 44,66 | 8,57 | 29,77 | 71,7 |
| I-16 | 57,42 | 7,20 | 22,10 | 57,58 | 7,25 | 22,39 | 80,6 |
| I-17 | 40,89 | 7,61 | 27,67 | 41,15 | 7,89 | 27,43 | 73,4 |
| I-18 | 46,93 | 7,85 | 24,08 | 46,93 | 7,88 | 24,33 | 71,1 |
| I-19 | 54,46 | 7,18 | 21,32 | 54,11 | 6,81 | 21,04 | 53,1 |
| I-20 | 55,52 | 7,28 | 20,15 | 55,69 | 7,19 | 19,98 | 52,3 |
| I-21 | 49,68 | 8,10 | 32,78 | 49,39 | 8,29 | 32,92 | 66,6 |
| I-22 | 50,69 | 7,47 | 26,31 | 50,91 | 7,59 | 26,38 | 27,8 |

TABLE 2-continued

Elementary analysis data and yield of the compounds I

| Designated Compounds | Found, % C | H | N | Calculated, % C | H | N | Yield, (%) |
|---|---|---|---|---|---|---|---|
| I-23 | 58,28 | 6,41 | 22,28 | 58,04 | 6,49 | 22,56 | 70,7 |
| I-24 | 49,86 | 8,31 | 14,73 | 51,05 | 8,57 | 14,88 | 66,5 |
| I-25 | 55,82 | 9,28 | 13,22 | 55,53 | 9,32 | 12,95 | 58,7 |
| I-26 | 58,73 | 9,82 | 11,27 | 58,99 | 9,90 | 11,47 | 71,0 |
| I-27 | 68,98 | 11,74 | 7,33 | 68,70 | 11,53 | 7,28 | 53,2 |
| I-28 | 69,67 | 11,71 | 7,02 | 69,85 | 11,73 | 6,79 | 68,6 |
| I-29 | 62,45 | 7,35 | 11,03 | 62,38 | 7,25 | 11,19 | 78,2 |
| I-30 | 63,61 | 7,57 | 10,85 | 63,61 | 7,63 | 10,60 | 57,4 |
| I-31 | 57,98 | 6,32 | 10,42 | 58,20 | 6,39 | 10,44 | 85,7 |
| I-32 | 47,68 | 5,33 | 8,72 | 47,43 | 5,21 | 8,51 | 33,0 |
| I-33 | 65,36 | 6,31 | 7,36 | 65,61 | 6,29 | 7,29 | 71,1 |
| I-34 | 54,06 | 7,98 | 13,77 | 53,98 | 8,05 | 13,99 | 52,3 |
| I-35 | 49,84 | 8,50 | 12,55 | 49,53 | 8,31 | 12,84 | 57,2 |
| I-36 | 45,25 | 7,53 | 13,10 | 45,54 | 7,65 | 13,28 | 65,4 |
| I-37 | 53,28 | 9,25 | 13,57 | 53,44 | 8,97 | 13,85 | 28,2 |
| I-38 | 60,17 | 10,02 | 10,96 | 60,43 | 10,14 | 10,84 | 70,6 |
| I-39 | 63,84 | 7,59 | 10,39 | 63,61 | 7,63 | 10,60 | 74,9 |
| I-40 | 59,32 | 7,04 | 10,21 | 59,56 | 6,78 | 9,92 | 85,9 |
| I-41 | 48,45 | 5,51 | 22,99 | 48,99 | 5,58 | 23,28 | 73,7 |
| I-42 | 53,13 | 8,69 | 13,45 | 53,44 | 8,97 | 13,85 | 51,4 |
| I-43 | 60,08 | 9,89 | 10,98 | 60,43 | 10,14 | 10,84 | 77,6 |
| I-44 | 63,25 | 7,33 | 10,36 | 63,61 | 7,63 | 10,60 | 62,5 |
| I-45 | 59,32 | 6,67 | 10,21 | 59,56 | 6,78 | 9,92 | 83,2 |
| I-46 | 49,31 | 5,29 | 8,38 | 48,99 | 5,58 | 8,16 | 68,4 |
| I-47 | 48,34 | 8,67 | 24,53 | 48,54 | 8,73 | 24,26 | 85,5 |
| I-48 | 53,98 | 9,25 | 21,13 | 53,71 | 9,52 | 20,88 | 40,2 |
| I-49 | 57,88 | 10,06 | 18,45 | 57,61 | 10,11 | 18,32 | 55,3 |
| I-50 | 69,72 | 11,74 | 10,37 | 69,47 | 11,91 | 10,57 | 61,5 |
| I-51 | 61,55 | 7,04 | 18,13 | 61,26 | 7,28 | 17,86 | 46,8 |
| I-52 | 46,98 | 8,18 | 20,36 | 47,27 | 8,43 | 20,68 | 69,1 |
| I-53 | 44,22 | 7,73 | 20,97 | 44,43 | 7,99 | 22,21 | 43,7 |
| I-54 | 66,42 | 6,72 | 19,15 | 66,34 | 6,95 | 19,34 | 38,1 |
| I-55 | 46,13 | 7,16 | 16,37 | 45,97 | 7,33 | 16,08 | 54,2 |
| I-56 | 55,86 | 6,44 | 13,22 | 55,72 | 6,55 | 13,00 | 89,1 |
| I-57 | 49,87 | 7,76 | 14,63 | 49,99 | 7,69 | 14,57 | 95,0 |
| I-58 | 58,27 | 6,42 | 9,27 | 58,43 | 6,54 | 9,09 | 69,1 |
| I-59 | 36,67 | 6,33 | 18,28 | 36,97 | 6,20 | 18,48 | 39,5 |
| I-60 | 63,05 | 8,91 | 11,22 | 63,29 | 8,79 | 11,07 | 14,3 |
| I-61 | 58,17 | 6,31 | 22,39 | 58,05 | 6,49 | 22,56 | 54,3 |
| I-62 | 56,66 | 8,72 | 25,13 | 56,78 | 8,93 | 24,94 | 18,5 |
| I-63 | 61,04 | 5,72 | 17,64 | 61,26 | 5,99 | 17,86 | 19,4 |
| I-64 | 46,74 | 5,56 | 13,65 | 46,89 | 5,85 | 13,67 | 54,2 |
| I-65 | 41,35 | 7,42 | 24,05 | 41,14 | 7,48 | 23,99 | 68 |
| I-66 | 41,70 | 8,51 | 31,95 | 41,37 | 8,10 | 32,16 | 42 |
| I-67 | 37,50 | 7,52 | 21,48 | 37,29 | 7,82 | 21,74 | 81 |
| I-68 | 43,52 | 7,33 | 15,02 | 43,62 | 7,69 | 15,26 | 78 |
| I-69 | 52,03 | 9,40 | 24,30 | 52,15 | 9,63 | 24,33 | 92 |

TABLE 3
PMR SPECTRA OF DERIVATIVES OF COMPOUND I

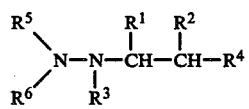

| Designated compounds | Solvent | Chemical shifts δ, p.p.m. $CHR^1$ | $CHR^2$ | $H_{R^3}$ | $H_{R^4}$ | $H_{R^5}$ | $H_{R^6}$ | SSIC, J, Hz $CHR^1$—$CHR^2$ | Balance |
|---|---|---|---|---|---|---|---|---|---|
| I-1 | CDCl$_3$ | 3,57 | 2,71 | 5,9 | 3,69 | 2,51 | 2,51 | 8,1 | |
| I-2 | CDCl$_3$ | 3,53 | 2,71 | 6,3(NH) 2,79(CH$_3$) | 3,67 | 2,45 | 2,45 | 7,5 | 7,8(NHCH$_3$) |
| I-3 | CDCl$_3$ | 3,62 | 2,76 | 8,5(NH) 6,9-7,5(C$_6$H$_5$) | 3,67 | 2,55 | 2,55 | 7,4 | |
| I-4 | CDCl$_3$ | 3,62 | 2,73 | 8,45(NH); 7,40(C$_6$H$_4$); 3,68(COOCH$_3$); 3,62(CH$_2$N); 2,77(CH$_2$C); 2,55(N(CH$_3$)$_2$) | 3,68 | 2,55 | 2,55 | 7,4 | |
| I-5 | CDCl$_3$ | 3,99 | 2,92 | 7,8(NH) 3,05(CH$_3$) | 3,64 | 2,46 | 2,46 | 8,0 | 5,0(NHCH$_3$) |
| I-6 | CDCl$_3$ | 4,01 | 2,93 | 7,9(NH); 4,0-4,4(CH$_2$N); 5,1-5,3(CH$_2$); 5,7-6,2(CH) | 3,65 | 2,47 | 2,47 | 7,8 | — |
| I-7 | CDCl$_3$ | 4,08 | 2,98 | 9,7(NH) 7,1-7,7(C$_6$H$_5$) | 3,66 | 2,55 | 2,55 | 7,6 | — |
| I-8 | CDCl$_3$ | 3,27 | 2,43 | 6,0(NH) 2,52(CH$_3$) | 3,86(CH$_2$) 0,99(CH$_3$) | 2,23 | 2,23 | 7,8 | 4,7(NHCH$_3$) 7,0(CH$_2$CH$_3$) |
| I-9 | CDCl$_3$ | 4,03 | 2,93 | 7,9(NH); 3,9-4,2(CH$_2$N); 5,1-5,3(CH$_2$) 5,7-6,2(CH) | 4,15(CH$_2$) 1,26(CH$_3$) | 2,53 | 2,53 | 8,0 | 7,0(CH$_2$CH$_3$) |
| I-10 | CDCl$_3$ | 4,13 | 3,00 | 9,8(NH); 7,0-7,7(C$_6$H$_5$) | 4,17(CH$_2$) 1,27(CH$_3$) | 2,61 | 2,61 | 7,8 | 6,7(CH$_2$CH$_3$) |
| I-11 | CDCl$_3$ | 3,31 | 3,11(CH) 1,19(CH$_3$) | 5,7 | 3,73 | 2,45 | 2,45 | 6,0 | 8,5(CH$_3$—CH) |
| I-12 | CDCl$_3$ | 3,28 | 3,11(CH) 1,17(CH$_3$) | 6,4(NH) 2,78(CH$_3$) | 3,67 | 2,44 | 2,44 | 6,5 | 4,8(CH$_3$—NH) 6,4(CH$_3$—CH) |
| I-13 | CDCl$_3$ | 3,8 | 3,5(CH) 1,22(CH$_3$) | 8,1(NH); 4,25(CH$_2$N); 5,2-6,0(CH=CH$_2$) | 3,67 | 2,46 | 2,51 | — | 5,0(NH—CH) 6,7(CH—CH$_3$) |
| I-14 | CDCl$_3$ | 3,9 | 3,5(CH) 1,24(CH$_3$) | 9,9(NH) 7,1-7,6(C$_6$H$_5$) | 3,67 | 2,51 | 2,56 | — | 6,7(CH—CH$_3$) |
| I-15 | CDCl$_3$ | 3,32 | 2,35 | 6,70(NH) | 7,3 6,8 | 2,35 | 2,35 | 7,8 | 3,6(CH$_3$—NH) |

TABLE 3-continued

PMR SPECTRA OF DERIVATIVES OF COMPOUND I

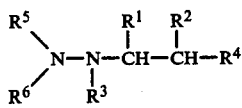

| Designated compounds 1 | Solvent 2 | Chemical shifts δ, p.p.m. | | | | | | SSIC, J, Hz | |
|---|---|---|---|---|---|---|---|---|---|
| | | $CHR^1$ 3 | $CHR^2$ 4 | $H_{R^3}$ 5 | $H_{R^4}$ 6 | $H_{R^5}$ 7 | $H_{R^6}$ 8 | $CHR^1$—$CHR^2$ 9 | Balance 10 |
| I-16 | CDCl₃ | 3,66 | 2,67 | 2,61(CH₃) 8,6(NH) 6,9–7,5(C₆H₅) | 6,5 5,7 | 2,58 | 2,58 | 7,0 | — |
| I-17 | CDCl₃ | 4,06 | 2,82 | 7,9(NH) | 6,4 6,1 | 2,52 | 2,52 | 7,5 | — |
| I-18 | CDCl₃ | 4,08 | 2,84 | 3,11(CH₃) 8,0(NH); 4,2–4,4(CH₂N); 5,1–5,3(CH₂); 5,75–6,2(CH) | 5,7 6,3 | 2,54 | 2,54 | 7,8 | — |
| I-19 | CDCl₃ | 4,16 | 2,89 | 9,8(NH) 7,1–7,6(C₆H₅) | 6,2 5,5 | 2,62 | 2,62 | 7,5 | — |
| I-20 | CDCl₃ | 3,8 | 1,22(CH₃) 3,66(CH) | 9,9(NH) 7,2–7,6(C₆H₅) | 6,1 5,7 | 2,56 | 2,56 | — | 6,7(CH—CH₃) |
| I-21 | CDCl₃ | 3,34 | 2,68 | 6,2(NH) 2,66(CH₃) | — | 2,38 | 2,38 | 6,0 | 5,1(CH₃—NH) |
| I-22 | CDCl₃ | 3,86 | 2,98 | 7,9(NH); 4,11(α-CH₂); 4,9–5,3(=CH₂); 5,5–6,0(=CH) | — | 2,43 | 2,43 | 6,7 | — |
| I-23 | CDCl₃ | 3,56 | 2,84 | 8,5(NH) 6,9–7,5(C₆H₅) | — | 2,57 | 2,57 | 6,4 | — |
| I-24 | CDCl₃ | 3,58 | 2,69 | 2,13 | 3,69 | 2,51 | 2,51 | 7,0 | — |
| I-25 | CDCl₃ | 3,58 | 2,69 | 2,47(α-CH₂); 1,60(β-CH₂); 0,91(CH₃) | 3,67 | 2,50 | 2,50 | 6,9 | 7,2(NCH₂CH₂) 6,7(CH₂CH₃) |
| I-26 | CDCl₃ | 3,58 | 2,68 | 2,50(α-CH₂); 1,6(β-CH₂); 1,3(γ,δ-CH₂); 0,87(CH₃) | 3,67 | 2,49 | 2,49 | 7,0 | — |
| I-27 | CDCl₃ | 3,58 | 2,69 | 2,49(α-CH₂); 1,6(β-CH₂); 1,3(γ,δ-CH₂); 0,87(CH₃) | 3,69 | 2,47 | 2,47 | 7,0 | — |
| I-28 | CDCl₃ | 3,58 | 2,69 | 2,48(α-CH₂); 1,6(β-CH₂); 1,3(C—CH₂—C); 0,86(CH₃) | 3,67 | 2,49 | 2,49 | 7,0 | — |
| I-29 | CDCl₃ | 3,71 | 2,80 | 7,3–7,6 | 3,71 | 2,53 | 2,59 | 7,0 | — |
| I-30 | CDCl₃ | 3,47 | 2,58 | 3,73(CH₂); 7,2(C₆H₅) | 3,58 | 2,29 | 2,29 | 7,0 | — |
| I-31 | CDCl₃ | 3,69 | 2,80 | 6,8–7,4 | 3,62 | 2,36 | 2,36 | 6,8 | — |
| I-32 | CDCl₃ | 3,70 | 2,78 | 7,49 7,40 | 3,70 | 2,51 | 2,51 | 6,7 | — |
| I-33 | — | — | — | — | — | — | — | — | — |
| I-34 | CDCl₃ | 3,58 | 2,75 | 7,0–7,3(CHCO) 6,2–6,4(CH=CH) 5,55–5,7(CH=CH) | 3,71 | 2,55 | 2,55 | 7,8 | — |
| I-35 | D₂O | 3,69 | 2,62 | 3,20(β-CH₂) 2,56(α-CH₂) | 3,64 | 3,21 | 3,21 | 6,8 | 5,0(CH₂CH₂) |
| I-36 | CDCl₃ | 3,62 | 2,59 | 3,73 | 3,69 | 2,64 | 2,64 | 6,8 | — |
| I-37 | CDCl₃ | 3,27 3,51 | 3,00(CH) 1,23(CH₃) | 2,13 | 3,67 | 2,44 | 2,50 | 8,0 5,4 | 6,7(CH—CH₃) 13,0(N—CHR¹) |
| I-38 | CDCl₃ | 3,27 3,53 | 3,07(CH) 1,24(CH₃) | 2,49(α-CH₂); 1,6(β-CH₂); 1,3(γ,δ-CH₂); 0,87(CH₃) | 3,64 | 2,42 | 2,49 | 9,0 5,0 | 6,7(CH—CH₃) 12,8(N—CHR¹) |
| I-39 | CDCl₃ | 3,40 3,64 | 3,16(CH) 1,22(CH₃) | 7,3–7,6 | 3,68 | 2,49 | 2,49 | 8,0 5,2 | 6,7(CH—CH₃) |
| I-40 | CDCl₃ | 3,5 | 1,27(CH₃) 3,2(CH) | 6,9–7,4 | 3,69 | 2,40 | 2,43 | — | 6,7(CH—CH₃) |
| I-41 | CDCl₃ | 3,5 | 3,0–3,3(CH) 1,25(CH₃) | 7,45 | 3,71 | 2,49 | 2,49 | — | 7,0(CH—CH₃) |
| I-42 | CDCl₃ | 3,56 | 2,64 | 2,11 | 4,13(CH₂) 1,24(CH₃) | 2,51 | 2,51 | 6,9 | 6,8(CH₂—CH₃) |
| I-43 | CDCl₃ | 3,56 | 2,62 | 2,47(α-CH₂); 1,56(β-CH₂); 1,3(γ,δ-CH₂); 0,84(CH₃) | 4,11(CH₂) 1,24(CH₃) | 2,49 | 2,49 | 6,9 | 6,7(CH₂—CH₃) |
| I-44 | CDCl₃ | 3,70 | 2,76 | 7,2–7,6 | 4,13(CH₂) 1,25(CH₃) | 2,51 | 2,51 | 7,0 | 6,6(CH₂—CH₃) |

TABLE 3-continued

PMR SPECTRA OF DERIVATIVES OF COMPOUND I

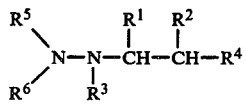

| Designated compounds 1 | Solvent 2 | Chemical shifts δ, p.p.m. | | | | | | SSIC, J, Hz | |
|---|---|---|---|---|---|---|---|---|---|
| | | CHR¹ 3 | CHR² 4 | $H_{R^3}$ 5 | $H_{R^4}$ 6 | $H_{R^5}$ 7 | $H_{R^6}$ 8 | CHR¹—CHR² 9 | Balance 10 |
| I-45 | CDCl₃ | 3,76 | 2,82 | 6,9–7,4 | 4,17(CH₂) 1,29(CH₃) | 2,44 | 2,44 | 7,5 | 6,7(CH₂—CH₃) |
| I-46 | CDCl₃ | 3,70 | 2,76 | 7,40 | 4,15(CH₂) 1,26(CH₃) | 2,49 | 2,49 | 7,0 | 6,7(CH₂—CH₃) |
| I-47 | CDCl₃ | 3,63 | 2,62 | 2,17 | 6,5 5,7 | 2,54 | 2,54 | 6,9 | — |
| I-48 | CDCl₃ | 3,60 | 2,60 | 2,51(α-CH₂); 1,60(β-CH₂); 0,96(CH₃) | 6,6 5,8 | 2,51 | 2,51 | 6,9 | — |
| I-49 | CDCl₃ | 3,58 | 2,56 | 2,49(α-CH₂); 1,6(β-CH₂); 1,3(β,γ-CH₂); 0,86(CH₃) | 6,6 5,7 | 2,49 | 2,49 | 6,9 | — |
| I-50 | CDCl₃ | 3,60 | 2,58 | 2,51(α-CH₂); 1,6(β-CH₂); 1,3(C—CH₂—C); 0,84(CH₃) | 6,4 5,4 | 2,51 | 2,51 | 6,9 | — |
| I-51 | DMSO | 3,56 | 2,49 | 7,4 | 7,4 6,9 | 2,42 | 2,42 | 6,8 | — |
| I-52 | D₂O | 3,73 | 2,67 | 2,44(α-CH₂) 3,22(β-CH₂) | — | 3,27 | 3,27 | 7,0 | 6,0(CH₂CH₂) |
| I-53 | CDCl₃ | 3,60 | 2,56 | 6,3 6,0 | 3,72 | 2,65 | 2,65 | 7,0 | — |
| I-54 | CDCl₃ | 3,65 | 2,89 | 7,2–7,6 | — | 2,55 | 2,55 | 6,6 | — |
| I-55 | CDCl₃ | 4,33 (CH) 3,04 (COOCH₃) | 3,44 | 6,20(NH) 2,70(CH₃) | 3,64 | 2,50 | 2,42 | 6,3 | 3,9(CH₃—NH) |
| I-56 | CDCl₃ | 4,49 (CH) 3,73 (COOCH₃) | 3,74 2,56 | 8,4(NH) 6,9–7,6(C₆H₅) | 3,73 | 2,69 | 2,60 | 8,4 | — |
| I-57 | CDCl₃ | 4,40 (CH) 3,73 (COOCH₃) | 3,56 2,49 | 6,3(NH) 3,16(α-CH₂) | 3,73 | 2,56 | 2,47 | 8,2 3,8 | 6,0(NH—CH₂) 16,1(COCH₂) |
| I-58 | CDCl₃ | 4,62 (CH) 3,76 (COOCH₃) | 3,78 2,50 | 7,3–7,7 | 3,76 | 2,58 | 2,58 | — | — |
| I-59 | D₂O | 3,93 | 2,73 | 3,00 | — | 2,51 | 2,51 | 6,9 | |
| I-60 | CDCl₃ | 4,11 | 2,98 | 9,77(NH) 7,1–7,6(C₆H₅) | 4,07(α-CH₂) 1,6(β-CH₂); 1,3(C—CH₂—C); 0,89(CH₃) | 2,58 | 2,58 | 6,5 | |
| I-61 | CDCl₃ | 3,56 | 2,84 | 8,5(NH) 6,9–7,6(C₆H₅) | — | 2,60 | 2,60 | 6,6 | — |
| I-62 | CDCl₃ | 3,52 | 2,80 | 2,75(α-CH₂); 2,51(β-CH₂); 1.09(CH₃) | — | 2,56 | 2,56 | 6,7 | 7,2(CH₂—CH₃) |
| I-63 | CDCl₃ | 3,71 | 2,93 | 6,9–7,3 | — | 2,48 | 2,48 | 6,8 | — |
| I-64 | CDCl₃ | 3,48 | 2,41 | 8,38(NH) 7,0(C₆H₅) | — | 2,27 | 2,27 | — | — |
| I-65 | DMSOd₆ | 3,33 | 2,49 | 6,09(NH₂) | 12,1(COOH) | 2,39 | 2,39 | 7,0 | |
| I-66 | CDCl₃ | 3,56 | 2,74 | 5,6(NH₂) | — | 2,57 | 2,57 | 6,0 | |
| I-67 | CDCl₃ | 3,38 | 2,71 | 8,5(NH₂) | 3,76 | 3,08 | 3,08 | 6,0 | |
| I-68 | CDCl₃ | 4,67 4,12 | 2,53 | 7,94(NH) 5,87; 5.23; 5,11(CH=CH₂) 4,23(CH₂) | 3,72 3,70 | 2,62 | 2,53 | 2,0 8,8 | 16,8 (²JCH₂) |
| I-69 | CDCl₃ | 3,56 | 2,62 | 6,40(NH); 3,18(α-CH₂) 1,5(β-CH₂); 1,3(γ-CH₂); 0,92(CH₃) | 6,96 5,62 | 2,47 | 2,47 | 6,7 | |

TABLE 4

Antiarrythmic activity of the proposed compounds on a model of arrythmia caused by administration of calcium chloride (antogonism to calcium) in experiments with mice

| Designated compounds | Intraperitonial dose (mg/kg) | Dose of calcium chloride causing in animals under experiment (mg/kg) arrythmia | Death |
|---|---|---|---|
| 1 | 2 | 3 | 4 |
| Quinidine | — | 85,0 | 100,0 |
|  | 3 | 126,9 | 136,0 |
|  | 10 | 120,8 | 133,5 |
| Procaineamide | 10 | 116,0 | 120,0 |
|  | 30 | 127,0 | 138,0 |
| I-1 | 5 | 118,5 | 149,0 |
|  | 15 | 124,4 | 138,3 |
| I-2 | 5 | 112,0 | 128,5 |
|  | 15 | 124,5 | 140,6 |
| I-3 | 5 | 86,7 | 97,0 |
|  | 25 | 124,7 | 130,0 |
| I-4 | 5 | 86,0 | 110,0 |
|  | 25 | 103,7 | 115,0 |
| I-5 | 5 | 87,5 | 100,5 |
|  | 25 | 127,3 | 131,4 |
| I-6 | 5 | 97,9 | 110,4 |
|  | 25 | 100,9 | 113,7 |
| I-7 | 5 | 132 | 135,6 |
|  | 15 | 107,5 | 138,0 |
|  | 25 | 90,0 | 113,0 |
| I-8 | 5 | 99,4 | 112,0 |
|  | 25 | 123,2 | 124,6 |
| I-9 | 5 | 91,8 | 107 |
|  | 25 | 104,8 | 116,5 |
| I-10 | 5 | 102,0 | 108,8 |
|  | 15 | 115,8 | 125,7 |
| I-11 | 5 | 100,3 | 147 |
|  | 15 | 130,7 | 136,3 |
| I-12 | 5 | 106,0 | 110,0 |
|  | 15 | 128,3 | 130,5 |
| I-13 | 5 | 117,3 | 136,5 |
|  | 15 | 126,0 | 138,0 |
| I-14 | 5 | 96,4 | 114,1 |
|  | 15 | 85 | 101,0 |
| I-15 | 5 | 97,8 | 109 |
|  | 15 | 100,7 | 108,5 |
| I-16 | 5 | 92,0 | 115,3 |
|  | 15 | 102,5 | 125,0 |
| I-17 | 5 | 87,5 | 138 |
|  | 15 | 102,0 | 115 |
| I-18 | 5 | 127 | 160,5 |
|  | 15 | 153 | 168 |
| I-19 | 5 | 98,3 | 112,0 |
|  | 15 | 110,5 | 130,0 |
| I-20 | 5 | 102 | 123 |
|  | 15 | 106,4 | 118,6 |
| I-21 | 5 | 87,5 | 111,5 |
|  | 25 | 113,6 | 128,0 |
| I-22 | 5 | 92,5 | 108,0 |
|  | 25 | 130,0 | 146,0 |
| I-23 | 5 | 86 | 101,3 |
|  | 25 | 117,7 | 119,0 |
| I-24 | 5 | 108,0 | 132,0 |
|  | 15 | 116,5 | 140,3 |
| I-25 | 5 | 105,1 | 112,3 |
|  | 25 | 77,0 | 95,0 |
| I-26 | 5 | 111,3 | 138,0 |
|  | 15 | 107,6 | 140,0 |
| I-27 | 5 | 92,7 | 118,0 |
|  | 15 | 109,0 | 120,6 |
| I-28 | 5 | 90,1 | 108 |
|  | 25 | 133,8 | 143 |
| I-29 | 5 | 97,6 | 109,5 |
|  | 25 | 140,2 | 142,0 |
| I-30 | 5 | 94,0 | 120,5 |
|  | 15 | 102,0 | 125,0 |
| I-31 | 5 | 88,5 | 109,0 |
|  | 15 | 100,5 | 112,5 |
| I-32 | 5 | 90,3 | 105,5 |
|  | 15 | 100,0 | 110,0 |
| I-33 | 5 | 87,5 | 108,6 |
|  | 15 | 111,0 | 132,5 |
| I-34 | 5 | 108,4 | 130,0 |
|  | 15 | 110,5 | 136,0 |
| I-35 | 5 | 102,3 | 120 |
|  | 15 | 105,8 | 132,5 |
| I-36 | 5 | 94,0 | 113,6 |
|  | 15 | 98,6 | 118,5 |
| I-37 | 5 | 100 | 132,0 |
|  | 15 | 123 | 138,0 |
| I-38 | 5 | 102,0 | 115,8 |
|  | 15 | 96,5 | 120,0 |
| I-39 | 5 | 88,7 | 111,3 |
|  | 15 | 100,0 | 121,5 |
| I-40 | 5 | 93,5 | 115,0 |
|  | 15 | 103,3 | 118,6 |
| I-41 | 5 | 90,6 | 110,0 |
|  | 15 | 102,5 | 122,0 |
| I-42 | 5 | 87,5 | 112,0 |
|  | 15 | 103,0 | 115,0 |
| I-43 | 5 | 94,0 | 105,0 |
|  | 15 | 108,5 | 120,3 |
| I-44 | 5 | 101,0 | 120,0 |
|  | 15 | 98,5 | 126,0 |
| I-45 | 5 | 95,0 | 112,5 |
|  | 15 | 102,8 | 125,0 |
| I-46 | 5 | 98,0 | 105,0 |
|  | 15 | 100,0 | 118,3 |
| I-47 | 5 | 103 | 118 |
|  | 15 | 108 | 125 |
| I-48 | 5 | 88 | 101,8 |
|  | 15 | 95,3 | 109 |
| I-49 | 5 | 101,3 | 120,5 |
|  | 15 | 108,6 | 136,8 |
| I-50 | 5 | 102,4 | 118,0 |
|  | 15 | 118,6 | 142,5 |
| I-51 | 5 | 88,7 | 105,5 |
|  | 15 | 93,5 | 112,0 |
| I-52 | 5 | 93 | 112,0 |
|  | 15 | 97,6 | 123,6 |
| I-53 | 5 | 98,5 | 132,0 |
|  | 15 | 121,0 | 138,5 |
| I-54 | 5 | 108,3 | 130,0 |
|  | 15 | 102,5 | 133,0 |
| I-55 | 5 | 88,7 | 112,5 |
|  | 15 | 111,5 | 135,0 |
| I-56 | 5 | 92,4 | 108,5 |
|  | 15 | 102,0 | 128,0 |
| I-57 | 5 | 103,5 | 115,0 |
|  | 15 | 132,6 | 150,0 |
| I-58 | 5 | 97,0 | 112,0 |
|  | 15 | 100,5 | 118,5 |
| I-59 | 5 | 93,4 | 108,6 |
|  | 15 | 112,5 | 130,0 |
| I-60 | 5 | 90,8 | 132,5 |
|  | 15 | 107,5 | 130,8 |
| I-61 | 5 | 105,0 | 128,8 |
|  | 15 | 102,6 | 130,0 |
| I-62 | 5 | 96,5 | 120,5 |
|  | 15 | 98,7 | 118,5 |
| I-63 | 5 | 101,5 | 117,3 |
|  | 15 | 112,3 | 128,0 |
| I-64 | 5 | 98 | 147 |
|  | 15 | 141,7 | 163 |

TABLE 5

Acute toxicity of the proposed compounds in intraperitonial administration to white mice (mg/kg)

| Designated compounds | LD$_{50}$ (mg/kg) | Relative toxicity to quinidine |
|---|---|---|
| 1 | 2 | 3 |
| I-1 | 2080 (1434–3016) | 13,3 |
| I-2 | 2300 (1703–3105) | 14,7 |
| I-3 | 1350 (900–2025) | 8,6 |
| I-4 | 8000 51,3 | |

TABLE 5-continued

Acute toxisity of the proposed compounds in intraperitonial administration to white mice (mg/kg)

| Designated compounds 1 | LD50 (mg/kg) 2 | Relative toxicity to quinidine 3 |
|---|---|---|
| I-5 | 3950 (2724–5727,5) | 25,3 |
| I-6 | 3200 (2370,4–4320) | 20,5 |
| I-7 | 2100 (1272,7–3465) | 13,4 |
| I-8 | 1870 (1317–2655,4) | 11,9 |
| I-9 | 1780 (1271,4–2492) | 11,4 |
| I-10 | 1800 (1285–2520) | 11,5 |
| I-11 | 1850 (1360,3–2516) | 11,8 |
| I-12 | 1270 (940–1715) | 8,1 |
| I-13 | 1230 (878,5–1722) | 7,8 |
| I-14 | 1960 (1420–2705) | 12,5 |
| I-15 | 3600 (2400–5400) | 23 |
| I-16 | 925 (637,9–1341,2) | 5,9 |
| I-17 | 2850 (2035,7–3990) | 18,3 |
| I-18 | 2900 (2000–4205) | 18,6 |
| I-19 | 1750 (1287–2380) | 11,2 |
| I-20 | 1340 (957–1876) | 8,6 |
| I-21 | 1800 (1286–2520) | 11,5 |
| I-22 | 1450 (1021–2059) | 9,3 |
| I-23 | 1680 (1200–2352) | 10,7 |
| I-24 | 1300 (896–1885) | 8,3 |
| I-25 | 1750 (1296,3–2362,5) | 11,2 |
| I-26 | 630 (477–832) | 4,0 |
| I-27 | 2380 (1587–1740) | 15,2 |
| I-28 | 6150 (3967,7–9532,0) | 39,4 |
| I-29 | 3500 (2447,5–5005) | 22,4 |
| I-30 | 1200 (827,5–1740) | 7,6 |
| I-31 | 1600 (1127–2272) | 10,2 |
| I-32 | 1680 (1120–2520) | 10,7 |
| I-33 | 2850 (2065–3933) | 18,2 |
| I-34 | 980 (700–1372) | 6,2 |
| I-35 | >3000 | >19,2 |
| I-36 | 1380 (945–2015) | 8,8 |
| I-37 | 810 (595–1101) | 5,1 |
| I-38 | 1930 (1270–2934) | 12,3 |
| I-39 | 1750 (1232–2485) | 11,2 |
| I-40 | 1400 (1000–1960) | 8,0 |
| I-41 | 2430 (1620–3645) | 15,5 |
| I-42 | 2375 (1605–3515) | 15,2 |
| I-43 | 1460 (1021–2088) | 9,3 |
| I-44 | 1650 (1031–2640) | 10,5 |
| I-45 | 1480 (1121–1954) | 9,4 |
| I-46 | 1500 (1035–2175) | 9,6 |
| I-47 | >3000 | >19,2 |
| I-48 | 1700 (1300–2210) | 10,9 |
| I-49 | 960 (662–1392) | 6,1 |
| I-50 | >3000 | >19,2 |
| I-51 | 3150 (2250–4410) | 20,1 |
| I-52 | >3000 | >19,2 |
| I-53 | 1880 (1315–2688) | 12,0 |
| I-54 | 1030 (644–1648) | 6,6 |
| I-55 | 2300 (1643–3220) | 14,7 |
| I-56 | 3200 (2208–4576) | 20,5 |
| I-57 | >3000 | >19,2 |
| I-58 | >3000 | >19,2 |
| I-59 | 1800 (1125–2880) | 11,5 |
| I-60 | 2425 (1672–3316) | 15,5 |
| I-61 | 1250 (893–1750) | 8,0 |
| I-62 | 930 (650–1330) | 5,9 |
| I-63 | 1850 (1294–2646) | 11,8 |
| I-64 | 1750 (1346–2275) | 11,2 |
|  | 156 (111,4–218,4) | 1 |
|  | 290 (145–580) | 1,85 |

What is claimed is:

1. A substituted 3-hydrazinopropionate of the general formula $$\begin{array}{c} R^5 \\ \phantom{R^5}\diagdown \\ \phantom{R^5}N-N-CH-CH-R^4, \\ \phantom{R^5}\diagup \phantom{XX} | \phantom{XX} | \phantom{XX} | \\ R^6 \phantom{XXX} R^3 \phantom{XX} R^1 \phantom{XX} R^2 \end{array}$$

wherein
  $R^1$ and $R^2$ are individually selected from the group consisting of H, $C_1$–$C_4$ alkyl and $COOCH_3$;
  $R^3$ is $$-\underset{\underset{O}{\|}}{C}-N\diagup^{R^7}_{\diagdown R^8} \quad \text{or} \quad -\underset{\underset{S}{\|}}{C}-N\diagup^{R^7}_{\diagdown R^8}$$

wherein
  $R^7$ and $R^8$ are individually selected from the group consisting of H, $C_1$–$C_4$ alkyl, allyl and phenyl;
  $R^4$ is $-C\equiv N$ or $-COR^{10}$ in which $R^{10}$ is $OR^{11}$ wherein $R^{11}$ is selected from the group consisting of H, $C_1$–$C_8$ alkyl and alkali metal, or $NR^{12}R^{13}$ wherein $R^{12}$ and $R^{13}$ are individually selected from the group consisting of H and $C_1$–$C_4$ alkyl; and
  $R^5$ and $R^6$ are individually $C_1$–$C_4$ alkyl.

2. A substituted 3-hydrazinopropionate according to claim 1, wherein $R^1$ and $R^2$ are hydrogen; $R^3$ is $$-\underset{\underset{O}{\|}}{C}NHC_6H_5 \quad \text{or} \quad -\underset{\underset{S}{\|}}{C}NHCH_3;$$

$R^4$ is COOK or COONa; and $R^5$ and $R^6$ are methyl.

3. A substituted 3-hydrazinopropionate according to claim 1, wherein $R^3$ is $$-\underset{\underset{S}{\|}}{C}-N\diagup^{R^7}_{\diagdown R^8}.$$

4. A substituted 3-hydrazinopropionate according to claim 3, wherein $R^4$ is COONa.

* * * * *